United States Patent [19]
Blacklock et al.

[11] Patent Number: 5,695,334
[45] Date of Patent: Dec. 9, 1997

[54] BENDABLE AND CASTABLE POST AND CORE

[76] Inventors: Gordon D. Blacklock, 3321 Columbia N.E., Albuquerque, N. Mex. 87107; Americo Fernandes, #3 Carmarthen Blvd., Winnipeg, Manitoba, Canada, 43POW3

[21] Appl. No.: 571,239
[22] Filed: Dec. 8, 1995
[51] Int. Cl.⁶ .................................................. A61C 8/00
[52] U.S. Cl. ......................... 433/173; 433/213; 433/215
[58] Field of Search ................................. 433/173, 172, 433/215, 213

[56] References Cited

U.S. PATENT DOCUMENTS

| | | | |
|---|---|---|---|
| 4,431,416 | 2/1984 | Niznick | 433/174 |
| 4,645,453 | 2/1987 | Niznick | 433/173 |
| 4,758,161 | 7/1988 | Niznick | 433/173 |
| 5,073,110 | 12/1991 | Barbone | 433/173 |
| 5,316,477 | 5/1994 | Calderon | 433/173 |
| 5,350,301 | 9/1994 | DeBuck | 433/173 |
| 5,350,302 | 9/1994 | Marlin | 433/174 |
| 5,372,503 | 12/1994 | Elia | 433/215 |

FOREIGN PATENT DOCUMENTS 3110694  9/1982  Germany ......................... 433/173

*Primary Examiner*—John J. Wilson
*Attorney, Agent, or Firm*—Terrance L. Siemens

[57] ABSTRACT

Apparatus and method for producing a permanent metal post and core adjusted angularly in order to result in a prosthesis aligned in parallel relation to surrounding teeth and prostheses. A bendable post and core assembly is placed in a conventional anchor. The post is bent to a precise desired angle with respect to the core, and cemented in this position. A ceramic mold is formed around the cemented post and core. The post and core, which is preferably fabricated from a synthetic organic polymer which melts at a temperature below 1,400° F., is then heated and evacuated from the mold. A permanent post and core is then cast in the mold from a suitable material, such as gold. Optionally, a sleeve which is configured to slip over and closely conform to the post is employed, either to increase the diameter of the core prior to forming the mold, or to assist in fabricating the denture after the permanent post and core is completed.

5 Claims, 3 Drawing Sheets

BENDABLE AND CASTABLE POST AND CORE

BACKGROUND OF THE INVENTION

1. Field of the Invention

The present invention relates to a post and core assembly for dental implants. More particularly, the post and core assembly is constructed such that the post is bendable with respect to the core. This enables a dentist to adjust for misalignment from a vertical direction of the anchor which receives the post and core assembly. The post is tilted and cemented into a desired position. This modified post and core is employed to form a ceramic mold. The mold is heated to allow material forming the post and core to evacuate the mold. A permanent post and core is then cast in the evacuated mold.

In a further step, the post may be reattached to the core, if separated by breakage. The post is drilled to cooperate with the stub of the neck connecting the post and core, and is cemented into position.

As an option, a sleeve which slips over the post is provided. The sleeve is, in one use, installed prior to forming the mold. This increases the diameter and strength of the permanent core. In an alternative use, the sleeve is employed in forming a prosthesis or denture by a molding technique after fabrication of the permanent post and core.

2. Description of the Prior Art

When a denture is to be attached to the jaw of a patient, it must be properly aligned with the other teeth or implants so as to be parallel thereto. A problem arises when an anchor receiving the post and core is inserted into the jaw at an angle not corresponding to a direction resulting in parallel arrangement of the associated denture. This may arise because bone tissue capable of securely supporting the anchor is not located advantageously for appropriate placement of the anchor, or because it is simply too difficult to install appropriately.

It is possible to adjust for an anchor set out of parallel with respect to other teeth or dentures by causing the prosthesis to be mounted out of axial alignment with the anchor, and in the desired parallel position with respect to the other teeth. This may be accomplished by causing the post and core to accommodate the new orientation by being adjustable, or by incorporating a compensating misalignment within its own structure.

An example of the former approach incorporating a rotatably adjustable post and core assembly is shown in U.S. Pat. No. 5,316,477, issued to Luis O. Calderon on May 31, 1994. Calderon's post and core must have an anchor having a circular hole for receiving the core. By contrast, the present invention has a conventional hexagonal core which cooperates with a conventional anchor having a hexagonal hole. Also, the degree of tilt, or deviation from the axis of the post and core, is adjustable in the present invention.

An example of the latter compensating approach incorporating a rotatably adjustable post and core assembly employing reference marks is shown in U.S. Pat. No. 5,350,301, issued to Vincent De Buck on Sep. 27, 1994. The post and core are provided as two separate, subsequently united structures in this invention. By contrast with the present invention, no part is bendable into the desired position in the De Buck invention. Rather, in the De Buck device, an assembly incorporating a desired angle must be built up from individual components.

An even more complicated built up post and core assembly is described in U.S. Pat. No. 5,350,302, issued to Gerald M. Marlin on Sep. 27, 1994. Some of the components of the post and core assembly have screw bores and mounting cavities which are misaligned, so that the component can be screwed to a supporting component. A subsequently mounted member continues at an angle to the supporting component. The various components allow for progressive adjustment to suit conditions as successive components are assembled and oriented at new angles to their predecessors. Unlike the present invention, there is no bendable component.

U.S. Pat. No. 5,073,110, issued to Noram K. Barbone on Dec. 17, 1991, illustrates a post and core assembly wherein the post comprises the ball of a ball and socket joint. The anchor provides the socket. Unlike the present invention, which employs a conventional hexagonal core compatible with a conventional anchor having a hexagonal hole, the anchor of the Barbone device is configured to receive a ball. The Barbone anchor must be designed from the outset to cooperate with its associated post and core. Unlike the present invention, Barbone's apparatus is not bendable.

None of the above inventions and patents, taken either singly or in combination, is seen to describe the instant invention as claimed.

SUMMARY OF THE INVENTION

The present invention provides a post and core which both cooperates with a conventional anchor having a hexagonal socket for receiving the core, and also adjusts for angular misalignment by bending or tilting. De Buck notes that while thin necked extensions, which would encompass a post and core assembly, are known, they are felt not to be satisfactory, since the thin neck is susceptible to breaking. The present invention overcomes this problem by providing a method of forming a post and core of conventional stout necked construction by first forming a precisely aligned original. The original has a thin neck, and is easily bent to the desired angle.

The method comprises two principal steps. The original is formed, employing the novel bendable post and core assembly. To form the original, the core is inserted into the anchor. After observing resultant orientation of the axis of the post and core with the other teeth or dentures, the post is bent or tilted with respect to the core, and is glued in the desired position. This new position or angular orientation is quite precise, since the post is infinitely adjustable, unlike some prior art assemblies which incorporate predetermined increments of adjustability.

In the second principal step, the modified post and core is then removed from the patient, and a ceramic or cement mold is formed around it. The post and core is heated until the material forming it slumps and flows from the mold. A permanent post core assembly is then cast in the mold from a suitable permanent material.

The neck of the permanent post and core will be stouter than the original, lacking the thin section or neck which allowed the core to be tilted relative to the post in the original post and core. The glue employed to secure the core in its new position builds up the diameter of the neck. The cavity of the ceramic mold is larger due to the presence of the glue, and additional space is thus created to account for the stouter neck in the reproduced, permanent member.

This process is most applicable for dental practitioners preferring to work in a material such as gold. The original post and core is formed from a readily pliable, easily melted material, such as a suitable synthetic organic polymer or copolymer. Acetal copolymer has proved a preferable material. The material is easily evacuated from the ceramic mold by low temperature heating equipment, such as small electric ovens commonly employed in dental laboratories. For the purposes of this invention, low temperature materials will encompass those melting at temperatures below 1,400° F. This temperature is generally lower than metals employed to fabricate permanent post and core assemblies, such as gold, silver-palladium alloys, titanium, and the like.

A synthetic organic polymer or copolymer also assists in retaining usefulness of the post should this member break off at the neck. The idle end of the post, formerly located opposite the core, is drilled to provide a hole. With the newly drilled hole oriented downwardly, the post is placed over the stump left by the broken neck. The post is susceptible to being glued back to the core. Since this post and core is merely the original in a casting process, excessive weakness of the material is not a fatal defect, as would be the case in a permanent post and core.

In a further step which is employed if, in the judgment of the dental practitioner, the post and core assembly is not of sufficient diameter, the diameter of the post is increased by slipping a sleeve over the post. This is performed after the post is cemented or glued in its desired new angular orientation. If employed, the sleeve also reinforces the permanent post and core since it intercepts the core at a greater diameter compared to the diameter of the original core. This greater diameter will be reflected in the corresponding diameter of the permanent post and core cast from the mold.

In an alternative use, the sleeve is employed after fabrication of the permanent post and core to form the denture. Since the sleeve cooperates closely with the original post, it will also cooperate closely with the permanent post. The sleeve allows the denture to be slipped onto and removed from the post during fabrication of the denture, so that correct fit and orientation of the denture may be verified prior to fabrication.

The novel post and core assembly is compatible with conventional anchors and prostheses, and therefore, does not require fabrication of special anchors and prostheses. Preferably fabricated from a synthetic organic polymer or copolymer, the post and core is relatively easy and inexpensive to fabricate. It accepts ordinary glue, as well as molten dental wax, which may not be the case if it were fabricated from other materials, and is sufficiently inexpensive to discard. Some metals may be too expensive to discard, and separating hardened glue debris from the melted metal may prove difficult. Therefore, synthetic organic polymers and copolymers are preferred.

Accordingly, it is a principal object of the invention to provide a post and core in which the post is bendable with respect to the core.

It is another object of the invention to form a post and core which is readily melted by low heat for evacuation from a mold.

It is a further object of the invention that the post and core accept ordinary glue as well as dental wax.

Still another object of the invention is to enable ready use of the post should it break off the core.

An additional object of the invention is to provide a member for increasing the diameter of the post after the core is angularly aligned.

It is again an object of the invention to provide a method for forming a precisely angled post and core from a permanent material.

Yet another object of the invention is to provide a bendable post and core assembly which is compatible with conventional anchors and prostheses.

Still another object of the invention is to provide a member which cooperates with the post for increasing post diameter or for assisting in subsequent fabrication of a denture.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
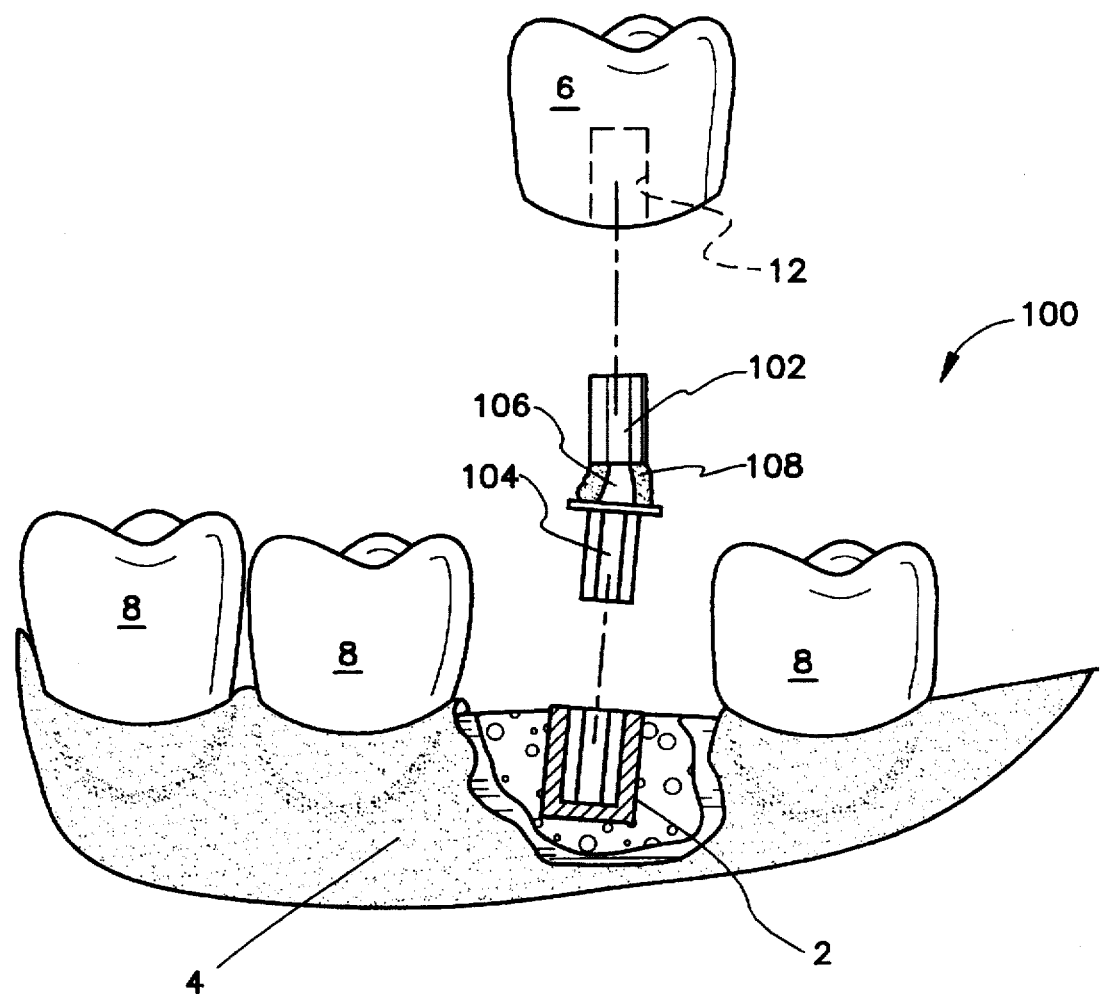
FIG. 1 is an environmental, partially cross sectional, side elevational view of the invention.

Turning now to FIG. 1 of the drawings, there is shown an anchor 2 embedded within bone tissue 4, oriented at an angle to the vertical. It is desired that a denture 6 be oriented vertically, as depicted herein, so that denture 6 is oriented parallel to other teeth or dentures 8. The problem solved by the present invention originates in the difficulty of orienting anchor 2 as desired within bone tissue 4. It is frequently the case that anchor 2 is out of parallel orientation with respect to neighboring teeth or dentures 8, as is illustrated in FIG. 1. When this misalignment occurs, the dental practitioner must correct in some way so that denture 6 is parallel to teeth or dentures 8.

Figure 5:
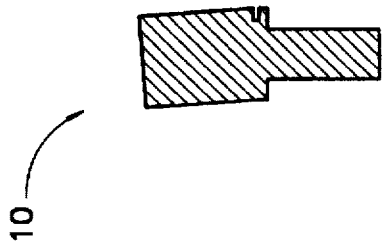
FIG. 5 is a cross sectional view of a permanent post and core assembly resulting from the novel method.

This is accomplished by providing a bendable and castable post and core assembly 100. Post and core assembly 100 is carefully fabricated to reflect the desired angle, and then is employed as an original in a casting process. Additionally, a machined metal reproduction could be made using a computerized scanning process and reproducing it with a computer controlled milling process. The casting process produces a permanent post and core assembly 10 (see FIG. 5) formed from a permanent material, such as gold, silver-palladium alloy, titanium, or the like. Post and core assembly 100 fits frictionally within anchor 2, and can be removed readily for adjustments during fabrication.

Post 102 is bent to a desired angle with respect to core 104. A narrow neck 106 is formed between post 102 and core 104, for joining post 102 to core 104, so that bending will occur at a desired point between post 102 and core 104. Thus, both post 102 and core 104 are able to be properly axially aligned with, respectively, denture 6 and anchor 2. Post and core assembly 100 is secured in the desired angled orientation by glue 108.

When post and core assembly 100 is deemed satisfactory, it may be employed in a subsequent casting operation to produce the permanent post and core assembly 10. It should be noted that the formerly narrow neck will be substantially stouter in the permanent post and core assembly due to dried glue or cement 108 (or a dental wax) increasing the overall diameter of post and core assembly 100 at neck 106.

Figure 2:
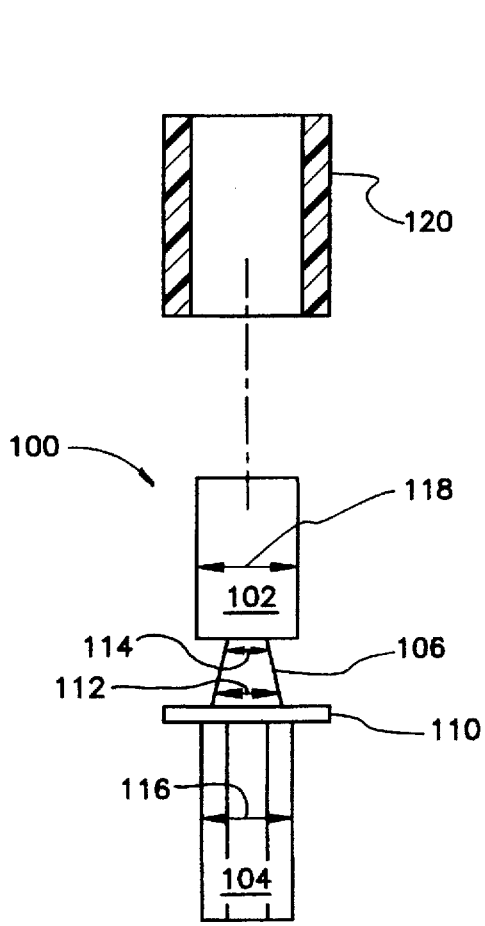
FIG. 2 is a side elevational, partially cross sectional view of the invention.

Characteristics of novel post and core assembly 100 are described with reference to FIG. 2. Post 102, core 104, and a base 110 are conventional. Neck 106 is preferably tapered to have a maximum diameter 112 proximate core 104 or base 110, and a minimum diameter 114 proximate post 102. It will be seen that even maximum diameter 112 is of less magnitude than core diameter 116 and post diameter 118. The narrower dimension assures that bending will occur at neck 106.

Figure 3:
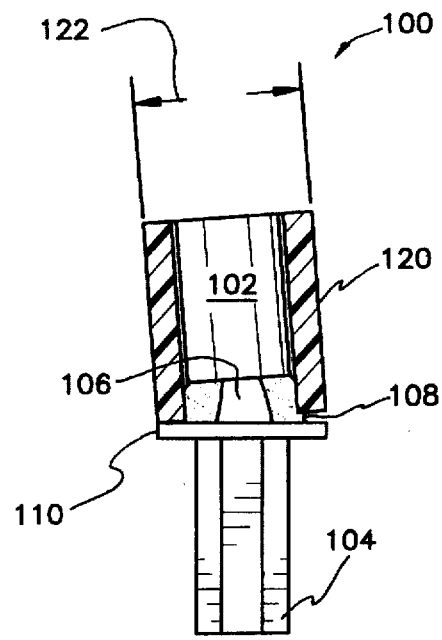
FIG. 3 is a side elevational, partially cross sectional view of the invention, and illustrating the assembled and glued condition.

A sleeve 120 is configured to cooperate closely with post 102. Sleeve 120 frictionally grips post 102, but may be readily manually removed. Sleeve 120 may be employed to increase the overall diameter 122 (see FIG. 3) of post 102. This arrangement may also assist in increasing solidity of attachment of post 102 to base 110.

Post and core assembly 100 is preferably formed from an inexpensive material which is flexible and melts at a low temperature. It must be physically and chemically stable in an oral environment. That is, it must not slump, decompose, dissolve, be toxic, or degrade when placed in the mouth. It must be flexible enough to bend at the neck. It must have sufficient tensile strength to retain post 102 united with core 104 under most circumstances of casual manipulation. It must have sufficient affinity for ordinary cements and glues employed by dental practitioners so that the cements and glues bond to the material. The material is also preferably soft and easily drilled.

The material should have a melting point well above body temperature, and below 1,400° F. This is a temperature representative of those routinely achieved in widely employed dental ovens for melting or burning out waxes and plastic materials employed in casting procedures. This temperature is also well below the melting points of metals and alloys in widespread use for permanent dental components. For the purposes of this invention, substances melting at temperatures below 1,400° F. will be referred to as melting at low temperatures.

Synthetic organic polymers, and in particular, acetal copolymer, have proved highly suitable as a constituent material. However, other materials, such as tin, may be found to yield satisfactory results.

In an alternative usage, best seen in FIG. 1, sleeve 120 may be employed in fabrication of denture 6. The close cooperation between the internal cavity of sleeve 120 and the exterior surface of post 102 may be exploited in a subsequent mold making or casting step to provide close cooperation between post 102 and a cavity 12 formed in denture 6.

In an alternative embodiment, the neck (not shown) need not be tapered, provided that the maximum diameter (not shown) of such a neck be of less magnitude than those of core diameter 116 and post diameter 118.

Figure 4:
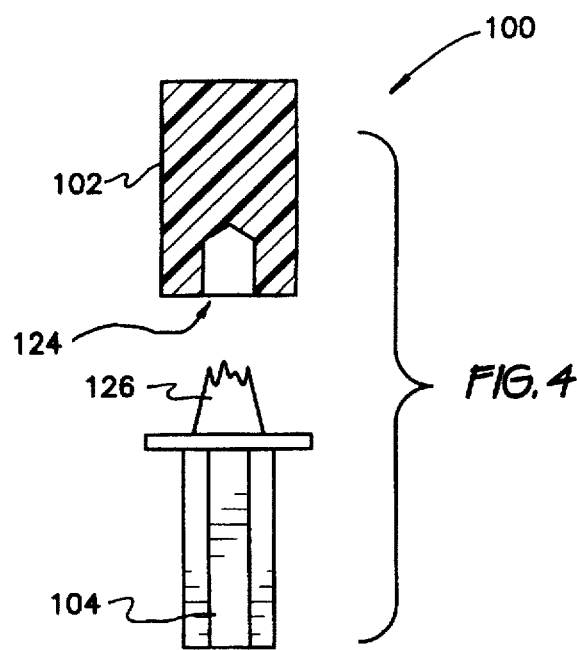
FIG. 4 is a side elevational, partially cross sectional view of the invention, illustrating an optional assembly step.

Utility of tapering of neck 106 is illustrated in FIG. 4. It is possible that excessive manipulation of post 102 will cause neck 106 (see FIG. 2) to break. Post 102 is still useful. Post 102 may be drilled, as indicated at 124, to cooperate with the substantial stump 126 left by neck 106. Taper of neck 106 helps assure that no projection remains on post 102. A drill bit (not shown) will therefore not tend to wander when drilling a new hole at 124.

Post 102 may then be set at an appropriate angle to core 104, and glued or cemented in this position. Thus, a tapered neck 106 assists in the event of breakage by assuring that the remaining stump 126 will cooperate with separated post 102. Of course, tapering may be oriented oppositely, so that stump 126 remains attached to post 102, drilling being performed on core 104.

Structure of a bendable and castable post and core assembly 100 has thus been described. The novel post and core assembly is employed to form a permanent post and core assembly 10 having a precise angle causing a denture 6 to be parallel to surrounding teeth or dentures 8 and being formed stoutly of a permanent material. The method of fabricating the permanent post and core assembly 10 is set forth as follows, and is summarized in FIG. 6, which is read from left to right.

The bendable and castable post and core assembly 100 is placed within a conventional anchor 2 inset into the jaw of a patient. The post 102 is bent into a desired angular position such that denture 6 will be parallel to other teeth or dentures 8 of the jaw of the patient. The post is cemented in the desired angular position.

Post and core assembly 100 is removed from the patient and a ceramic or cement mold (not shown) is formed in conventional manner around the bent and cemented post and core assembly 100. It should be noted that the mold could also be reproduced by copying the mold and shaping it from a block of metal with a computer controlled lathe. The mold is heated until the material of post and core assembly 100 melts and runs from the mold, or is evacuated from the mold by burning. Melted polymer and debris from dried glue or cement may be discarded.

The empty mold is then employed to cast a permanent post and core assembly by conventional method. Of course, it is preferred that post and core assembly 100 is melted at low temperature, so that conventional dental laboratory ovens may be employed in this step.

Figure 6:
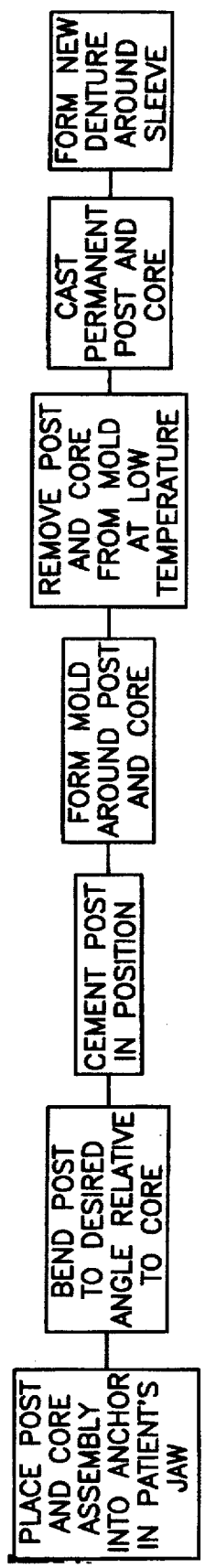
FIG. 6 is a block diagram summarizing the steps of a method of employing the novel post and core assembly.

Optionally, a sleeve 120 is placed over post 102 in order to increase the diameter and strength of the permanent post and core 10, as shown in the last step of the diagram of FIG. 6.

Figure 7:
FIG. 7 is a block diagram summarizing an optional step in the method of FIG. 6.

Alternatively, as summarized in FIG. 7, sleeve 120 is reserved for use in fabricating denture 6 in a prior, subsequent, or simultaneous operation. Denture 6 is fabricated in conventional fashion around sleeve 120, so that when partially fabricated, denture 6 may be installed onto and removed from post 102. Close fit between denture 6 and post and core assembly 100 is assured by employing sleeve 120, which has a predetermined close fit with post 102.

Denture 6 may be modified as required during fabrication, and correct fit and orientation of denture 6 at various degrees of completion may be verified prior to completion of fabrication of post and core assembly 100 or denture 6 or both.

It is to be understood that the present invention is not limited to the embodiments described above, but encompasses any and all embodiments within the scope of the following claims.

We claim:

1. A bendable and castable post and core assembly wherein the core is adjustably oriented with respect to the post, comprising:
   - a post having a post diameter dimension;
   - a core having a core diameter dimension; and
   - a neck joining said post to said core, said neck having a neck diameter dimension of magnitude less than that of said post diameter dimension and said core diameter dimension, said post and core assembly fabricated from a material of low melting temperature, said neck being tapered to have a maximum diameter proximate said core, and a minimum diameter dimension proximate said post, whereby a substantial stump will remain on said core, and no projection remains on said post, when said post breaks off said core.

2. The post and core according to claim 1, said material of low melting temperature being an organic polymer.

3. The post and core according to claim 2, said organic polymer being acetal copolymer.

4. The post and core according to claim 1, further comprising a separate sleeve having means defining an internal cavity configured and dimensioned to cooperate closely with said post, whereby said sleeve is slipped onto said post and is removable from said post.

5. A bendable and castable post and core assembly wherein the core is adjustably oriented with respect to the post, comprising:
   - a post and core member further comprising
       - a post having a post length dimension and a post diameter dimension,
       - a core having a core length dimension and a core diameter dimension, and
       - a neck joining said post to said core, said neck having a neck diameter dimension of magnitude less than that of said core diameter dimension and said post diameter dimension, said post and core assembly fabricated from acetal copolymer; and
   - a sleeve having means defining an internal cavity configured and dimensioned to cooperate closely with said post, whereby said sleeve is slipped onto said post and is removable from said post, said neck being tapered to have a maximum diameter proximate said core, and a minimum diameter dimension proximate said post, whereby a substantial stump will remain on said core, and no projection remains on said post, when said post breaks off said core.

* * * * *